US012025567B2

United States Patent
Lin et al.

(10) Patent No.: US 12,025,567 B2
(45) Date of Patent: Jul. 2, 2024

(54) ILLUMINATION SYSTEM, AN IMAGING SYSTEM, AND A METHOD FOR ILLUMINATION OF A SAMPLE IN A CONTAINER

(71) Applicant: IMEC VZW, Leuven (BE)

(72) Inventors: Ziduo Lin, Heverlee (BE); Abdulkadir Yurt, Heverlee (BE); Murali Jayapala, Kessel-Lo (BE); Geert Vanmeerbeeck, Keerbergen (BE)

(73) Assignee: IMEC VZW, Leuven (BE)

( * ) Notice: Subject to any disclaimer, the term of this patent is extended or adjusted under 35 U.S.C. 154(b) by 201 days.

(21) Appl. No.: 17/725,871

(22) Filed: Apr. 21, 2022

(65) Prior Publication Data
US 2022/0341853 A1 Oct. 27, 2022

(30) Foreign Application Priority Data
Apr. 23, 2021 (EP) .................................... 21170128

(51) Int. Cl.
*G01N 21/90* (2006.01)
*G01N 21/88* (2006.01)
(52) U.S. Cl.
CPC ..... *G01N 21/90* (2013.01); *G01N 2021/8845* (2013.01)
(58) Field of Classification Search
None
See application file for complete search history.

(56) References Cited

U.S. PATENT DOCUMENTS 4,682,023 A * 7/1987 Yoshida ............. G01N 21/9054
250/223 B
5,699,152 A * 12/1997 Fedor ................... G01N 21/909
356/240.1
(Continued)

FOREIGN PATENT DOCUMENTS

EP 2995676 A1 3/2016
WO WO-2019198669 A1 10/2019

OTHER PUBLICATIONS

Isikman, Serhan O., et al. "Lens-free optical tomographic microscope with a large imaging volume on a chip." Proceedings of the National Academy of Sciences 108.18 (2011): 7296-7301.
(Continued)

*Primary Examiner* — Tri T Ton
*Assistant Examiner* — Jarreas Underwood
(74) *Attorney, Agent, or Firm* — MOSER TABOADA

(57) ABSTRACT

An illumination system and method for illumination of a sample in a container is described herein. In some embodiments, the container includes a defined volume for receiving the sample. The illumination system includes, in some embodiments, at least one light source, a mask comprising an opaque portion, preventing light from passing through the mask, and an at least partially transparent portion, allowing light to pass through the mask. The illumination system can be adapted to be positioned such that the light generated by the light source, passing through the mask, illuminates the sample in the container. The light source and the mask are configured such that a shape, a size, and a position of a projection of the light passing through the mask, onto a plane of a bottom surface of the container, match a shape, a size, and a position of the bottom surface.

15 Claims, 8 Drawing Sheets

(56) References Cited

U.S. PATENT DOCUMENTS

2012/0147366 A1* 6/2012 Niedermeier .......... G01N 21/90
  356/240.1
2017/0145370 A1* 5/2017 Kato ..................... C12M 23/08

OTHER PUBLICATIONS

Allier, C. P., et al. "Video lensfree microscopy of 2D and 3D culture of cells." Imaging, Manipulation, and Analysis of Biomolecules, Cells, and Tissues XII. vol. 8947. International Society for Optics and Photonics, 2014.

Junhee Lee, Yeon Hwa Kwak, Se-Hwan Paek, Seungoh Han, Sungkyu Seo, "CMOS image sensor-based ELISA detector using lens-free shadow imaging platform", Sensors and Actuators B: Chemical, vol. 196, 2014, pp. 511-517, ISSN 0925-4005, https://doi.org/10.1016/j.snb.2014.02.059.

Kesavan, S. Vinjimore, et al. "High-throughput monitoring of major cell functions by means of lensfree video microscopy." Scientific reports 4.1 (2014): 1-11.

Solis, Leonardo et al. "Evaluation of a lens-free imager to facilitate tuberculosis diagnostics in MODS." Tuberculosis (Edinburgh, Scotland) vol. 97 (2016): 26-32. doi:10.1016/j.tube.2015.12.001.

Nicolas, J-D., et al. "Combined scanning X-ray diffraction and holographic imaging of cardiomyocytes." Journal of Applied Crystallography 50.2 (2017): 612-620.

Bernhardt, M., et al. "Correlative microscopy approach for biology using X-ray holography, X-ray scanning diffraction and STED microscopy." Nature communications 9.1 (2018): 1-9.

Scholz, Gregor, et al. "Continuous live-cell culture imaging and single-cell tracking by computational lensfree LED microscopy." Sensors 19.5 (2019): 1234.

Liu, Liwei, et al. "Design and experiment of a soft-edge aperture with high light energy utilization efficiency and uniformity." Applied Optics 59.18 (2020): 5348-5357.

European Search Report for application No. EP21170128, dated Oct. 6, 2021.

* cited by examiner

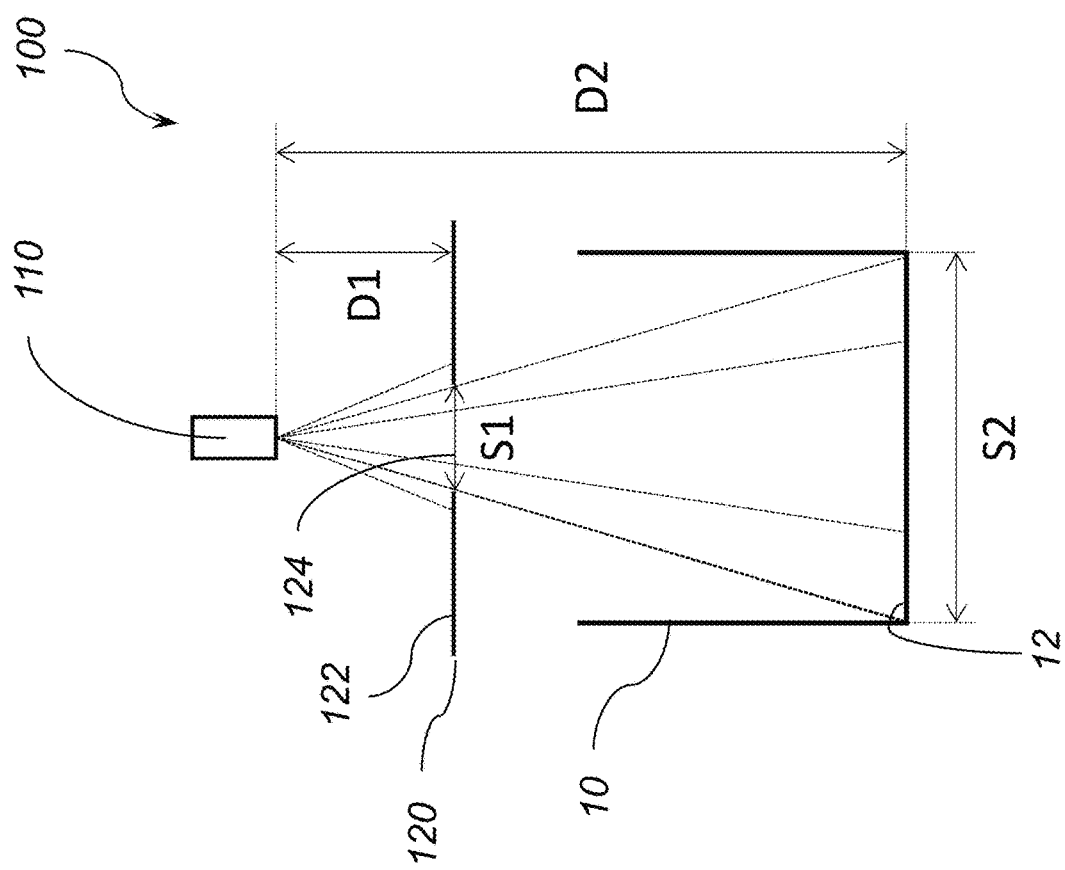
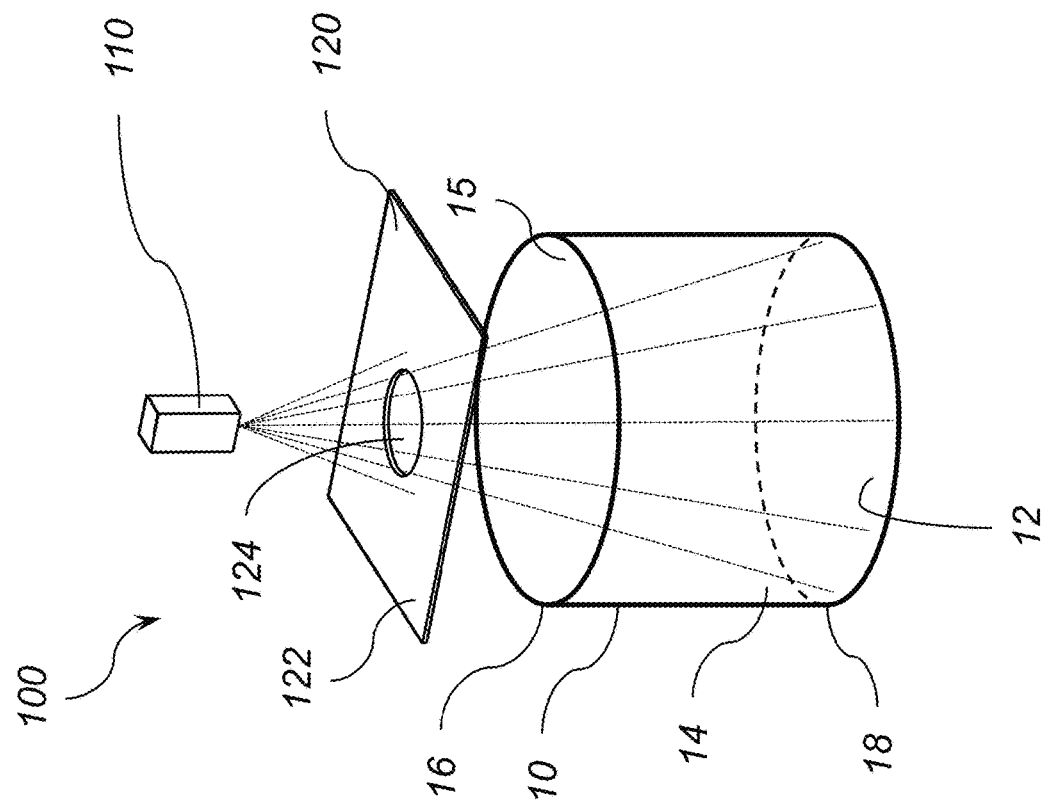
Fig. 2A
Fig. 2B

ILLUMINATION SYSTEM, AN IMAGING SYSTEM, AND A METHOD FOR ILLUMINATION OF A SAMPLE IN A CONTAINER

CROSS REFERENCE TO RELATED APPLICATIONS

This application claims priority to European Patent Application Serial No. 21170128.9, filed on Apr. 23, 2021, incorporated herein by reference in its entirety.

TECHNICAL FIELD

The present inventive concept relates to an illumination system and a method for illumination of a sample in a container such as a well of a microplate or a petri dish, and more specifically to an illumination system and a method suitable for application in imaging of a sample in a container.

BACKGROUND

In life science and medical research and industry, standard disposable containers such as well plates and petri dishes are intensively used for various activities including studies of cell culture, detection of antimicrobial activity, and reaction mixing. A variety of analytical tools, including imaging techniques, are required for monitoring and/or detecting parameters of interest, for example morphological features, of samples inside such containers.

With the currently available imaging solutions, the images of samples inside well plates and petri dishes need to be manually acquired with traditional microscope by an operator in laboratory. However, traditional microscopes are not well suited for acquiring images from inside industry standard incubators given its bulky size and alignment sensitive optics. The approach is very labor intensive and real-time monitoring of samples in their native incubator environment is not practically feasible.

On the other hand, for a lot of applications such as cell culture growth, micro-organism colony detection, and in-vitro diagnostics, acquiring images outside an incubator is not ideal, and there is a need for an improved imaging technique capable of monitoring of samples inside the native incubator environment at higher efficiency, preferably in real-time. Development of such an imaging technique that can provide suitable image acquisition as well as sample illumination is challenging, not only due to the requirement of adaption to a form factor of the container, but also due to the requirements for high resolution, compactness, and robustness against environment.

SUMMARY

An objective of the present inventive concept is to mitigate, alleviate or eliminate one or more of the above-identified deficiencies in the art and disadvantages singly or in any combination.

These and other objectives are at least partly met by the invention as defined in the independent claims. Preferred embodiments are set out in the dependent claims.

According to a first aspect of the present inventive concept there is provided an illumination system for illumination of a sample in a container, such as a well of a microplate or a petri dish, the container comprising a bottom surface and side walls which together define a volume for receiving the sample, the illumination system comprising:
at least one light source being configured to generate light;
a mask arranged such that light from the light source impinges onto the mask, wherein the mask comprises an opaque portion, preventing light from passing through the mask, and an at least partially transparent portion, allowing at least part of the light from the light source to pass through the mask;
wherein the illumination system is adapted to be positioned at a first end of the container such that the light generated by the light source, passing through the mask, illuminates the sample in the container; and
wherein the at least one light source and the mask are configured for light generated by the at least one light source being passed through the mask such that a shape, a size, and a position of a projection of the light passing through the mask, onto a plane of the bottom surface arranged at a second end of the container, opposite to the first end, match a shape, a size, and a position of the bottom surface of the container.

By the term "container" is here meant any type of container that may be used within life science or medical research, in which samples may be stored, grown, and/or analyzed. The container has at least one open or openable end through which the sample may be introduced into the container. Further, the container allows for light to pass into and/or out from the container, either through an open end or through a transparent wall of the container, so as to allow for optical diagnostics of the sample to be made.

Given as non-limiting examples, the well may be made of a plastic or glass material. The container may be of a commercially available standard, or it may be custom-made. The container may be of reusable type. Alternatively, the container may be of disposable type. By way of example, the container may be, but is not limited to, a petri dish. The container may a stand-alone container, or it may alternatively be part of a larger structure such as a plate comprising an array of containers. Given as another non-limiting example, the container may be a well of a microplate, such as a well in a 4-well, 6-well, 8-well, 12-well, 24-well, 96-well, 384-well, or 1536-well plate.

By the term "light source" is here meant any unit, device and/or element at which light is generated. In this context the term "light" should be allowed a wider interpretation, not limited to visible electromagnetic radiation but may also include for example ultra-violet light and infra-red light. By way of example, the light source may be, but is not limited to a laser, a laser diode, a light emitting diode, or a combination thereof.

By the term "mask" is here meant any unit, device and/or element comprising an opaque portion that prevents light impinging onto one side of the mask from reaching certain locations on the other side of the mask, and further comprising an at least partially transparent portion that allows at least part of the light to reach other locations on the other side of the mask. By way of example, a mask may be, but is not limited to, a metal plate with a through hole, a transparent glass plate partially painted or otherwise provided with a non-transparent surface coating, or an arrangement of one or more optical components refracting and/or reflecting the light so as to only reach certain locations on the other side of the mask.

Given as another non-limiting example, the mask may comprise an electronic device with multiple cells wherein each of the cells may be individually programmable in terms of level of transparency. Thereby, portions with different levels of transparency may be dynamically provided to generate a mask. By way of example, such a mask may be based on liquid crystals. By the present arrangement, a mask with a geometrical shape that can be altered via electrical signals and thereby be adapted to containers of different shapes may be provided.

It should be understood that by a portion being "opaque" is here meant that the portion is opaque with respect to the light generated by the at least one light source. By way of example, the light source may generate light at one or more specific wavelength, and thus by a portion being "opaque" is here meant that the portion is opaque to at least these one or more wavelengths. A portion that is opaque to at least these one or more wavelengths may or may not be transparent or partially transparent to some other wavelengths, not generated by the light source.

Analogous, it should be understood that the term "transparent" is here meant transparent with respect to the light generated by the at least one light source.

The at least one light source and the mask are configured such that the shape, the size, and the position of the projection of the light passing through the mask, onto a plane of the bottom surface of the container, matches the shape, the size, and the position of the bottom surface of the container. In other words, the light passing through the mask travels such that the side walls of the container are not illuminated, and such that substantially the full bottom surface of the container is illuminated. It should be understood that by "substantially the full bottom surface" is here meant at least 50% of the area of the bottom surface, preferably 75% and more preferably 80% of the area of the bottom surface. Thus, matching the size of the projection of the light to the size of the bottom surface does not require a 100% perfect match. The illumination of the bottom surface is achieved, provided that a sample in the container does not constitute an opaque obstacle preventing the light to reach the bottom of the container.

The bottom surface of the container may have, but is not limited to, a circular, elliptical, squared, or rectangular shape. However, it should be noted that matching the shape of the projection of the light to the shape of the bottom surface does not require a 100% perfect match. By way of example, if the bottom surface has the shape of a circle, the projection of the light may be a circle but may alternatively have a slightly elliptical shape yet covering a major part of the bottom surface of the container but not reaching the side walls of the container. By way of further example, if the bottom surface is in the shape of a square, the projection of the light may be a square but may alternatively have a rectangular shape covering a major part of the bottom surface of the container but not reaching the side walls of the container.

Matching the position of the projection of the light to the position of the bottom surface of the container means positioning the projection of the light with respect to the bottom surface such that the geometrical center of the projection of the light substantially coincides with the geometrical center of the bottom surface. However, matching the geometrical centers does not require a 100% perfect match. A slight discrepancy between the two geometrical centers is also considered to be a match, provided that no light passing through the mask illuminates any of the side walls of the container but all light passing through the mask is directed towards the bottom surface of the container, covering a major part of the bottom surface of the container.

The illumination system may be described herein as being a separate system in which the container is not comprised. However, the illumination system may be adapted to function together with one or more specific types of containers having predetermined dimensions. Further, it is conceivable that there is provided a kit of parts comprising an illumination system for illuminating a sample in a container, and a container and/or a plate comprising an array of containers. The illumination system in the kit of parts may be adapted to function together with the type of container included in the kit of parts.

An advantage with the present inventive concept is that since illumination of the side walls of the container may be prevented, light reflections from the side walls may thus be avoided. If not avoided, light reflections from side walls may cause strong undesired interference. Upon imaging the sample in the container, such interference will cause disturbance such as excessive noise and local brightness saturation of the detector. Consequently, the image quality is jeopardized if such interference is not avoided. By the present arrangement light reflections from the side walls may be avoided, and an illumination source well suited to be used for imaging of samples inside containers, such as industry standard and non-standard well plates and petri dishes, may be provided.

Another advantage with the present inventive concept is that illumination of the full bottom surface of the container is provided. For a sample arranged at the bottom of the container the present inventive concept may thus provide illumination of the sample in its entirety. By the present arrangement, simultaneous image acquisition of the full sample may be facilitated.

According to an embodiment, the at least one light source and the mask are configured for the shape, the size, and the position of the projection of the light passing through the mask, onto the plane of the bottom surface of the container, to match the shape, the size, and the position of the bottom surface of the container, by a position of the at least one light source being adjustable relative to the container and/or a position of the mask being adjustable relative to the container and/or the at least one light source.

The at least one light source and the mask are configured such that the shape, the size, and the position of the projection of the light passing through the mask, onto a plane of the bottom surface of the container, may be adjusted to match the shape, the size, and the position of the bottom surface of the container. In other words, the light passing through the mask may be adjusted such that the side walls of the container are not illuminated, and such that the full bottom surface is illuminated. The illumination of the full bottom surface is achieved, provided that a sample in the container does not constitute an opaque obstacle preventing the light to reach the bottom of the container. By way of example, adjustment in order to match the light passing through the mask and being projected onto the bottom surface of the container may be made by translation of the mask and the at least one light source in planes parallel to the bottom surface of the container such that an output of the at least one light source and a center of the at least partially transparent portion of the mask are aligned along a common axis of the container. Subsequently, by translation of the mask along the axis, e.g. in a direction perpendicular to the bottom surface, the size of the projected light may be matched to the size of the bottom surface. Alternatively, or in combination with the translation, the size of the at least partly transparent portion of the mask may be adjusted in order to match the size of the projected light to the size of the bottom surface. It is further conceivable that also the angle of the mask with respect to the bottom surface may be adjustable, in order to match the size of the projected light to the size of the bottom surface.

An advantage with this embodiment is that the adjustment enables optimization of the matching of the illumination to the bottom surface of the container, such that illumination of the full sample may be ensured while avoiding illumination of the side walls.

Another advantage with this embodiment is that, because of the illumination being adjustable, the illumination system may be used as illumination source for a variety of different container types of different sizes. In this manner, a more versatile illumination system may be provided.

According to an embodiment, the opaque portion of the mask is made of a solid material and the at least partly transparent portion of the mask comprises a through hole.

By way of example, the solid material out of which the mask is made may be metal, plastic or any other suitable solid material. By way of further example, the mask may be made from a sheet of such solid material. The through hole may be cut out of the solid material by a knife, scissors, a laser or any other suitable cutting device. Alternatively, the solid material may be cast-molded into a single piece comprising the through hole.

An advantage with this embodiment is that manufacturing of masks may be easy to carry out and masks may thereby be provided at a low cost.

Another advantage with this embodiment is that the mask may be made from a wear-resistant material, such that a durable mask may be provided.

According to an embodiment, the mask is made of a solid, transparent material provided with at least one surface coating.

By the term "surface coating" is here meant an optical coating that may alter one or more optical property of light reaching the surface coating, such as intensity, phase, or wavelength. By way of example, the at least one surface coating may be opaque to the light generated by the light source. By the present arrangement, a portion of the mask to which the at least one surface coating is provided may form the opaque portion of the mask, and a portion of the mask to which the at least one surface coating is not provided may form the at least partially transparent portion. By way of example, the at least one surface coating may be, but is not limited to, a reflecting and/or absorbing surface coating.

By way of example, the solid, transparent material out of which the mask is made may be a plastic or glass material. By way of further example, the at least one surface coating may be applied by, but is not limited to, painting or spraying the coating onto a surface of the solid, transparent material.

An advantage with this embodiment is that it may allow a larger variety of shapes and functions of the mask to be made, and may as such be more flexible in terms of producing masks for different types and shapes of containers.

It should be understood that a mask may be realized also in other ways than the ones previously mentioned. Given as non-limiting examples, a mask with an opaque portion and an at least partially transparent portion may be realized by a plastic plate with transparent resin in the center and opaque resin surrounding the transparent resin, or by providing a doping profile in glass material or by providing a microstructure on a transparent surface.

According to an embodiment, the mask comprises a gradient filter providing a soft edge aperture at an edge of the at least partially transparent portion.

By way of example, a substrate of the gradient filter may be made of a transparent material, such as a plastic or glass material. By way of further example, the substrate of the gradient filter may be provided with, but is not limited to, a surface coating of different light transmission properties at different portions of the gradient filter, thereby constituting a static soft edge aperture.

Alternatively, the gradient filter may comprise an electronic device with multiple cells wherein each of the cells may be individually programmable in terms of level of transparency. By the present arrangement, portions with different levels of transparency may be dynamically provided to optionally generate a mask with soft edges. Given as a non-limiting example, such a mask may be based on liquid crystals.

In case of a sharp edge aperture, the edges of the aperture may introduce additional diffraction around the perimeter of the bottom surface of the container. If such illumination is used for imaging, the diffraction will lead to noise and artifacts in the image. Depending on the width of the container and the area-of-interest for imaging, some diffraction may be acceptable especially for larger containers. For more narrow containers, however, diffraction from sharp edges of the mask may be a significant problem as diffraction may cover a major part of the area-of-interest to be imaged.

An advantage with the embodiment of a mask with a gradient filter providing a soft edge aperture is that diffraction of light that may otherwise occur around sharp edges may be avoided. Reduction or elimination of light diffraction at the mask edges may further reduce disturbing interference inside the container, thereby providing an illumination system suitable for imaging of samples in containers.

According to an embodiment, the mask comprises at least one lens arranged to direct the light being passed through the mask onto the bottom surface of the container.

An advantage with this embodiment is that diffracted light originating from sharp edges of the mask may be filtered out, thereby not reaching into the container. Consequently, a source of disturbing interference may thereby be eliminated.

An advantage with this embodiment is that standard components can be used for the illumination system. No custom-made optical components such as gradient filters are required.

According to an embodiment, the illumination system comprises an intensity filter arranged in an optical path of the light generated by the light source being passed through the mask, the intensity filter comprising different absorption coefficients across a cross-sectional plane of the optical path, thereby configured to provide a uniform illumination intensity onto the bottom surface of the container.

The light being passed through a mask may provide inhomogeneous illumination. By way of example, illumination may be stronger in the center of an illuminated area and weaker close to the edges of the illuminated area.

An advantage with this embodiment is that the intensity filter may compensate for inhomogeneities in the illumination. In the present manner, a more homogeneous illumination of the sample may be provided.

According to an embodiment, the intensity filter is arranged on the mask.

An advantage with this embodiment is that a compact arrangement of the illumination system comprising the intensity filter is provided.

According to an embodiment, the mask is arranged to extend in a plane parallel to the plane of the bottom surface of the container.

An advantage is that a well-defined relation between the projection of light passing through the mask and the bottom surface of the container is provided. Thus, it may be easily ensured that the shape, the size, and the position of the projection of the light passing through the mask, onto a plane of the bottom surface of the container, matches the shape, the size, and the position of the bottom surface of the container.

According to an embodiment, a shape of the at least partially transparent portion of the mask matches the shape of the bottom surface of the container.

An advantage with this embodiment is that it may be easier to realize the shape of the mask if the shape of the mask is the same as the shape of the bottom surface of the container that is being matched.

According to an embodiment, the at least one light source and the mask are configured for the shape and the size of the projection of the light passing through the mask, onto the plane of the bottom surface of the container, to match a circular shape having a diameter in a range of 10 μm to 150 mm.

According to an embodiment, the at least one light source and the mask are configured for the shape and the size of the projection of the light passing through the mask, onto the plane of the bottom surface of the container, to match an elliptical shape.

According to an embodiment, the at least one light source and the mask are configured for the shape and the size of the projection of the light passing through the mask, onto the plane of the bottom surface of the container, to match a square shape having a size of a side in a range of 10 μm to 150 mm.

According to an embodiment, the at least one light source and the mask are configured for the shape and the size of the projection of the light passing through the mask, onto the plane of the bottom surface of the container, to match a rectangular shape.

According to an embodiment, the illumination system is configured for illumination of samples in an array of containers, by the at least one light source and the mask being configured to be jointly movable in relation to the array of containers for moving the at least one light source and the mask between positions configured to be associated with illumination of different containers in the array, or by the at least one light source being movable in relation to the mask, wherein the mask comprises a plurality of at least partially transparent portions configured to be associated with different containers in the array, or by the illumination system comprising a plurality of light sources and the mask comprising a plurality of at least partially transparent portions such that different pairs of one light source and one at least partially transparent portions are configured to be associated with different containers in the array.

Several industry standard containers are in the form of arrays of containers. As mentioned earlier, such arrays of containers may be microplates comprising a plurality of wells.

An advantage with this embodiment is that suitable illumination for a plurality of samples in the array of containers may be provided.

Another advantage with this embodiment is that such an illumination system may have the potential of being automated. By the present arrangement, either sequential or simultaneous illumination may be provided for the containers of the array of containers.

An advantage with this embodiment is that it may increase the speed of illumination of the samples in industry standard microplates. Hence, the present embodiment facilitates increased image acquisition speed, when used for imaging of the samples.

According to a second aspect of the present inventive concept there is provided an imaging system for imaging a sample in a container, the imaging system comprising:
  the illumination system according to the first aspect;
  a detector comprising an array of light sensitive areas;
  wherein the imaging system is further configured such that at least part of the light illuminating the sample is scattered by the sample, forming scattered light;
  wherein the imaging system is further configured to transmit the scattered light and non-scattered light, from the same light source, to the array of light sensitive areas, wherein the array of light sensitive areas is configured to detect an interference pattern formed by interference between the scattered light and the non-scattered light, so as to image the sample.

The term "imaging" of a sample is herein regarded to include also acquisition of the interference pattern. By acquisition of the interference pattern formed by interference between the scattered light from the sample and the non-scattered light, information about the three-dimensional shape of the sample is acquired in terms of a digital hologram. Such information enables generation of a visual image of the sample, by means of holographic reconstruction.

By the term "light sensitive area" is here meant an area reacting to light impinging onto the area, by generating an electrical signal as a response to the light intensity. An array of light sensitive areas may be arranged on a detector, configured to allow read-out of the electrical signals representing light for image acquisition. Given as non-limiting examples, light sensitive areas may be found on photodiodes, photo-multiplier tubes (PMT), and pixels on image detectors such as charge-coupled devices (CCD) and complementary metal oxide semiconductors (CMOS). By way of example, an array of light sensitive areas may be in the form of pixels on a CCD or CMOS sensor, but may alternatively comprise a plurality of any other type of light sensitive areas.

The imaging system may be described herein as being a separate system in which the container is not comprised. However, the imaging system may be adapted to function together with one or more specific types of containers having predetermined dimensions. Further, it is conceivable that there is provided a kit of parts comprising an imaging system for imaging a sample in a container, and a container and/or a plate comprising an array of containers. The imaging system in the kit of parts may be adapted to function together with the type of container included in the kit of parts.

An advantage of the imaging system described above is that it offers the capability of imaging samples inside industry standard and non-standard containers, such as petri dishes and wells of microplates, yet reducing or eliminating excessive noise, local brightness saturation of the detector and/or other artefacts caused by light reflections from the side walls of the container. As discussed in relation to the first aspect of the present inventive concept, such artefacts may otherwise jeopardize the image quality.

Another advantage of the imaging system described above is that it may provide high, sub-micron image resolution, which is a requirement in several applications in the fields of life science and medical research and industry.

Another advantage of the imaging system described above is that it may have the potential of being automated.

According to some embodiments, either sequential or simultaneous illumination may be provided for a plurality of the containers. The present arrangement may further have the potential of increasing the speed of illumination of the samples in containers, and thereby increasing image acquisition speed. Consequently, the efficiency in extracting information about the samples in the containers may be increased.

According to an embodiment, the at least one light source is configured to generate at least partially coherent light.

Coherent light may be advantageous as it improves the interference visibility. A coherent light source may be a laser. However, it should be understood that also partially coherent light may provide an interference pattern with sufficient visibility. A partially coherent light source may e.g. be a light emitting diode, LED, emitting light through a pinhole onto the sample in the container. A coherent light source may provide better interference visibility but may be more expensive while a partially coherent light source may provide a worse interference visibility but may be less expensive. The at least partially coherent light may create an interference pattern, formed by interference between light scattered by the sample and non-scattered light, at the array of light sensitive areas.

According to a third aspect of the present inventive concept there is provided a method for illumination of a sample in a container, such as a well of a microplate, the container comprising a bottom surface and side walls which together define a volume for receiving the sample, the method comprising:

generating, by at least one light source, light for illuminating the sample in the container, at a first end of the container;

passing light from the light source through a mask, wherein the mask comprises an opaque portion, preventing light from passing through the mask, and an at least partially transparent portion, allowing at least part of the light from the light source to pass through the mask;

wherein the at least one light source and the mask are configured for light generated by the at least one light source being passed through the mask such that a shape, a size, and a position of a projection of the light passing through the mask, onto a plane of the bottom surface arranged at a second end of the container, opposite to the first end, match a shape, a size, and a position of the bottom surface of the container.

Effects and features of the second and third aspects are largely analogous to those described above in connection with the first aspect. Embodiments mentioned in relation to the first aspect are largely compatible with the second and third aspects. It is further noted that the inventive concepts relate to all possible combinations of features unless explicitly stated otherwise.

Other objectives, features and advantages of the present inventive concept will appear from the following detailed disclosure, from the attached claims as well as from the drawings.

BRIEF DESCRIPTIONS OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

FIG. 2A illustrates an illumination system for illumination of a sample in a container with a bottom surface having a circular shape.

FIG. 2B illustrates a cross-sectional side view of the illumination system for illumination of a sample in a container.

DETAILED DESCRIPTION

In cooperation with attached drawings, the technical contents and detailed description of the present inventive concept are described thereinafter according to a preferable embodiment, being not used to limit the claimed scope. This inventive concept may be embodied in many different forms and should not be construed as limited to the embodiments set forth herein; rather, these embodiments are provided for thoroughness and completeness, and fully convey the scope of the inventive concept to the skilled person.

Figure 1:
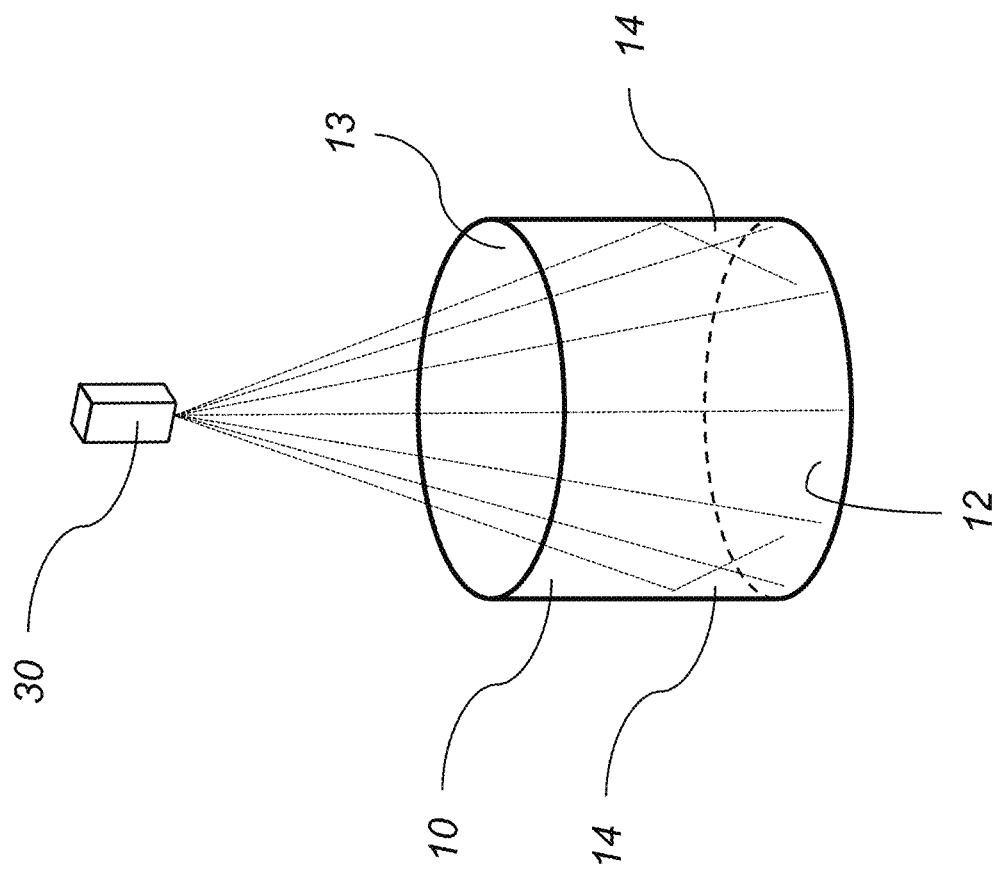
FIG. 1 illustrates the phenomenon of wall reflections when using a conventional light source for illumination of a container.

FIG. 1 illustrates the phenomenon of wall reflections when using a conventional light source for illuminating a sample in a container 10.

One challenging task when imaging samples in their native containers 10, such as wells of a microplate or a petri dish, is providing suitable illumination of the sample. By the use of a conventional light source 30 for introducing illumination light into the container 10, illumination light is reflected at the side walls 14 of the container 10. Some reflections will reach the bottom surface 12, resulting in strong interference between light being reflected at the side walls 14 and light that is not reflected at the side walls 14. Such interference is problematic for imaging of the sample, not least when the sample is imaged through the bottom surface 12 of the container 10. If holographic imaging is employed, interference from side wall reflections may cause artefacts such as detector saturation or excessive image noise, resulting in poor image quality. Hence, this type of illumination approach is not well suited for imaging of samples in the type of containers 10 mentioned, and side wall reflections need to be minimized or preferably eliminated. This is especially challenging in containers 10 with narrow openings 13 and tall side walls 14.

FIG. 2A illustrates an illumination system 100 for illumination of a sample in a container 10, according to an embodiment.

The container 10 in the present embodiment is a petri dish, however, it is conceivable that the container 10 alternatively may be of another type, such as a well in a microplate. The container 10 comprises a first end 16, which in the present embodiment is an open end, and a second end 18, which in the present embodiment is a closed end. The inner side of the closed second end 18 forms the bottom surface 12 of the container 10. Further, the container 10 comprises side walls 14 extending between the first end 16 and second end 18. The side walls 14 together with the bottom surface 12 define a volume 15 for receiving the sample.

The illumination system 100 comprises a light source 110 being configured to generate light, intended for illumination of the sample in the container 10. The light is here schematically illustrated by the dashed lines.

The illumination system 100 further comprises a mask 120 arranged such that light from the light source 110 impinges onto the mask 120.

The mask 120 comprises an opaque portion 122, preventing light from passing through the mask 120, and an at least partially transparent portion 124, allowing at least part of the light from the light source 110 to pass through the mask 120. In the present embodiment, the opaque portion 122 of the mask 120 is made of a metal plate and the at least partly transparent portion 124 of the mask 120 comprises a through hole through the metal plate. Alternatively, the mask 120 may be made of a plate of another solid material. By way of example, the mask 120 may be made of a plastic plate with a through hole. Further, the mask 120 may alternatively be made of a solid, transparent material provided with at least one surface coating to provide an opaque portion 122 and an at least partially transparent portion 124. It is conceivable that the transparent material may be a glass or plastic material, onto which a light blocking surface coating layer has been sprayed or painted. According to yet another alternative, the mask 120 may be formed from components that may be actively controlled to define the opaque portion 122 and the at least partially transparent portion 124 or at least part of the opaque portion 122 and the at least partially transparent portion 124 may be defined by the actively controlled components. Thus, the mask 120 may comprise an electronic device with multiple cells wherein each of the cells may be individually programmable in terms of level of transparency. By the present arrangement, portions with different levels of transparency may be dynamically provided to optionally generate a mask with soft edges. Given as a non-limiting example, such a mask 120 may be based on liquid crystals. In an embodiment, the mask 120 comprises a through hole or transparent portion surrounded by an electronic device with multiple cells such that an edge of the at least partially transparent portion 124 may be actively controlled.

The illumination system 100 is adapted to be positioned at the first end 16 of the container 10 such that the light generated by the light source 110, passing through the mask 120, illuminates the sample in the container 10. Positioning of the illumination system 100 at the first end 16 of the container 10 may be made manually by hand, or it may be automated. An actuator arrangement for adjusting the position of the light source 110 and mask 120 relative to the container 10 will be discussed in relation to FIG. 3.

Further, light source 110 and the mask 120 are configured for light generated by the light source 110 being passed through the mask 120 such that a shape, a size, and a position of a projection of the light passing through the mask 120, onto a plane of the bottom surface 12 arranged at a second end 18 of the container 10, opposite to the first end 16, match a shape, a size, and a position of the bottom surface 12 of the container 10.

The bottom surface 12 of the container 10 has a circular shape, in the present embodiment. Further, in the present embodiment, the mask 120 is arranged to extend in a plane parallel to the plane of the bottom surface 12 of the container 10. Thus, in order to match shape of the projection of light onto the plane of the bottom surface 12 with the shape of the bottom surface 12 itself, the geometrical shape of the at least partially transparent portion 124 of the mask 120 matches the geometrical shape of the bottom surface 12 of the container 10. In other words, the geometrical shape of the at least partially transparent portion 124 of the mask 120 is also circular.

The size of the container 10 may be different for different containers 10, but the illumination system 100 is configured such that the projection of the light onto the plane of the bottom surface 12 of the container 10 may be adapted to match a circular shape having a diameter in a range of 10 μm to 150 mm.

It is conceivable that the mask 120 may alternatively be arranged to be non-parallel with the bottom surface 12 of the container 10. In such a case, in order to match shape of the projection of light onto the plane of the bottom surface 12 with the shape of the bottom surface 12 itself, the geometrical shape of the at least partially transparent portion 124 of the mask 120 may have a different geometrical shape than the bottom surface 12 of the container 10.

The present arrangement enables illumination of a sample in the container 10 to be made without illumination light reaching the side walls 14, thereby avoiding side wall reflections. In the manner described above, an illumination system 100 suitable to be used for imaging of a sample in the container 10, may be provided.

FIG. 2B illustrates a cross-sectional side view of the illumination system 100 for illumination of a sample in a container 10, according to an embodiment.

Assume that the width of the bottom surface 12 is S2, and the width of the at least partially transparent portion 124 is S1. If the mask 120 is arranged to be parallel with the bottom surface 21 of the container 10, then positioning of the light source at a distance D2 from the bottom surface 12 would require the mask 120 to be positioned at distance D1 from the light source. The relation between the widths S1, S2 and distances D1, D2 may be described in the following way, for an ideal case:

$$\frac{S1}{S2} = \frac{D1}{D2}$$

It should be understood, however, that this ideal case may be an approximation of at least some real situations. For example, the ideal case described here assumes the light source to be a perfect point light source. This may not always be the case in a real situation. Further, if the container 10 is filled with a liquid, light entering the container 10 may be refracted to some degree at the liquid surface, depending on the difference in refractive indices between the liquid in the container 10 and the gas (typically air) outside the container 10. Such light refraction causing lensing effects are not taken into account in the ideal case. Further yet, if one or more lenses are introduced in the light path, the equation describing the ideal case may not apply.

Nevertheless, the above description of the ideal case may serve to provide a conceptual understanding of how a mask 120 and a light source 110 may be positioned, in order to achieve the matching of the projected light onto the bottom surface 12. For some real situations it may also serve as a good approximation.

Figure 3:
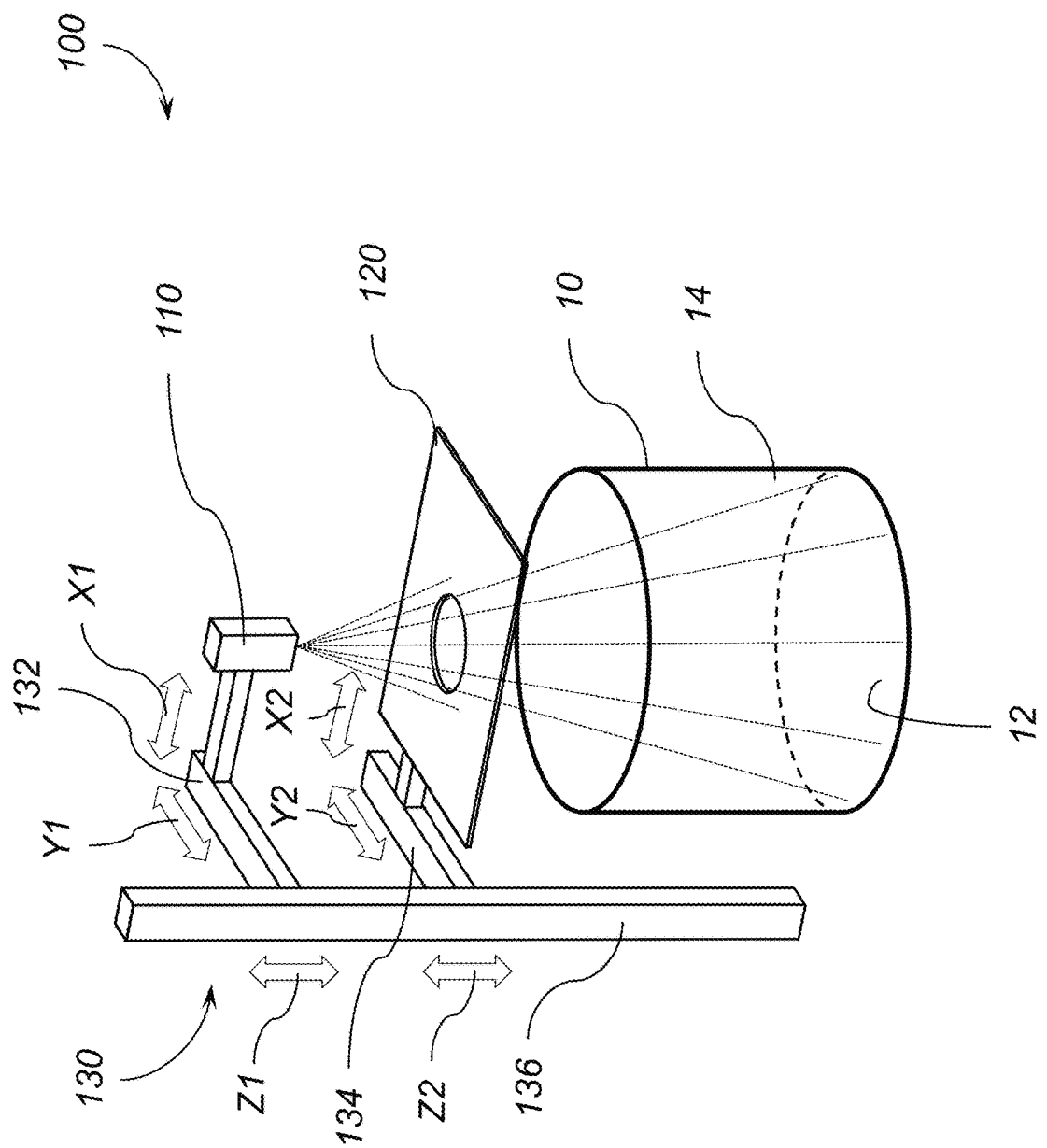
FIG. 3 illustrates an actuator arrangement for adjusting the position of the light source and mask of the illumination system relative to the container.

FIG. 3 illustrates an actuator arrangement 130 for adjusting the position of the light source 110 and mask 120 of the illumination system 100 relative to the container 10, according to an embodiment.

The actuator arrangement 130 comprises a light source actuator arm 132 configured to hold and move the light source 110, and a mask actuator arm 134 configured to hold and move the mask 120. The light source actuator arm 132 and the mask actuator arm 134 are arranged to independently move the light source 110 and the mask 120 in two perpendicular directions in the horizontal plane, X1 and Y1 for the light source 110, and X2 and Y2 for the mask 120.

The light source actuator arm 132 and the mask actuator arm 134 are movably arranged on a main actuator shaft 136. By moving the light source actuator arm 132 and the mask actuator arm 134 along the main actuator shaft 136, the position of the light source 110 and the mask 120 may independently be moved also in the vertical direction, Z1 for the light source 110 and Z2 for the mask 120. Movement of the arms 132, 134 may be achieved by electrically controlled step motors. However, it is conceivable that also other means for moving the arms 132, 134 may be possible.

In the manner described above, the position of the light source 110 and the position of the mask 120 may be independently adjustable relative to the container 10 and to each other. By the present arrangement, the shape, the size, and the position of the projection of the light passing through the mask 110, onto the plane of the bottom surface 12 of the container 10, may be adjusted to match the shape, the size, and the position of the bottom surface 12 of the container 10. Further, the present arrangement may allow the light projection to be adjusted to fit different containers 10 with bottom surfaces 12 of different sizes.

Figure 4A:
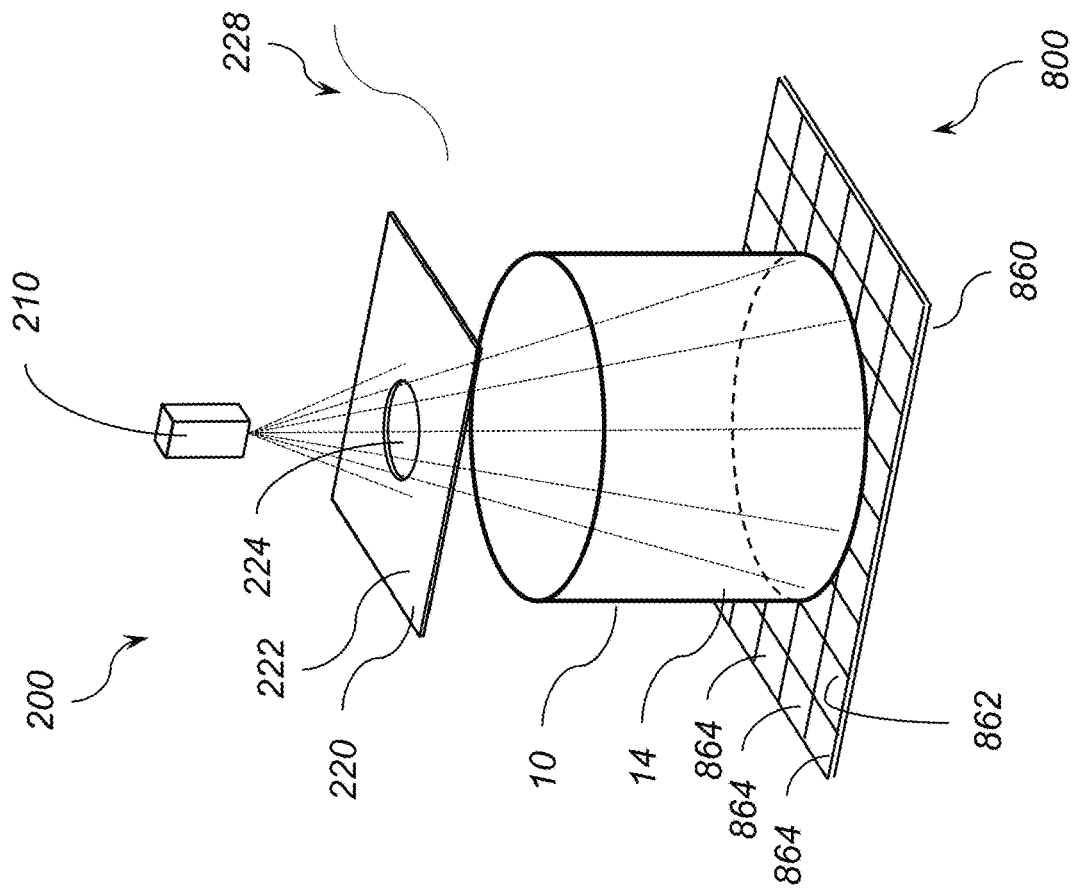
FIG. 4A illustrates an imaging system comprising the illumination system with a sharp edged mask, for illumination of a sample in the container.

FIG. 4A illustrates an imaging system 800 comprising the illumination system 100 for illumination of a sample in the container 10, according to an embodiment.

The illumination system 100 comprises a light source 110 and a mask 120 configured such that the projection of the light onto a plane of the bottom surface 12 of the container 10, matches the bottom surface 12 of the container 10. In the present manner, a sample in the container 10 may be illuminated by the light from the light source, yet illumination of the side walls 14 may be avoided. At least part of the light illuminating the sample is scattered by the sample, forming scattered light.

The imaging system 800 further comprises a detector 860 comprising an array 862 of light sensitive areas 864. The detector 860 in the present embodiment is an array of charge-coupled devices (CCD), however the detector may alternatively be of another type, for example an array of complementary metal oxide semiconductor (CMOS) sensors.

The detector 860 is arranged below the bottom surface 12 of the container 10, with the array 862 of light sensitive areas 864 facing the bottom surface 12 of the container 10.

Scattered light from the sample and non-scattered light, from the same light source 110, is transmitted to the array 862 of light sensitive areas 864. An interference pattern is formed by interference between the scattered light and the non-scattered light in the plane of the array 862, and the array 862 of light sensitive areas 864 is configured to detect the interference pattern, so as to image the sample.

By detection and acquisition of the interference pattern formed by interference between the scattered light from the sample and the non-scattered light, information about the three-dimensional shape of the sample is acquired in terms of a digital hologram. Such information enables generation of a visual image of the sample, by means of holographic reconstruction. The imaging system 800 offers the capability of imaging samples containers 10, such as petri dishes and wells of microplates, by holographic imaging, and at the same time reducing excessive noise, and other artefacts caused by light reflections from the side walls 14 of the container 10. The imaging system 800 as described above may further provide high, sub-micron image resolution, which is often a requirement in applications in the fields of life science and medical research and industry.

As mentioned in relation to FIG. 2A, the mask 120 of the illumination system 100 is made of a metal plate in which the at least partly transparent portion 124 of the mask 120 comprises a through hole through the metal plate. A through hole will provide a sharp edge 127 between the opaque portion 122 and the at least partially transparent portion 124, as schematically illustrated by a step in FIG. 4A. The sharp edge 127 may give rise to light diffraction when light from the light source passes through the mask 120. There may be circumstances under which the diffracted light may reach the perimeter of the bottom surface 12 of the container 10. Diffraction from sharp edges 127 of the mask 120 may be acceptable in some cases, especially for containers 10 with a large width of the opening 13. For narrow openings 13 however, diffraction from sharp edges 127 of the mask 120 may cause image noise or other artifacts affecting a large portion of an area-of-interest for imaging. For such situations alternative embodiments may be advantageous.

It should be understood that the imaging system 800 may allow the illumination system to be interchanged or adapted such that different illumination systems may be used in the imaging system 800 for imaging of samples for example in different types of containers. It is however conceivable that according to other embodiments an imaging system may have a fixed illumination system, dedicated for a specific type of container.

Figure 4B:
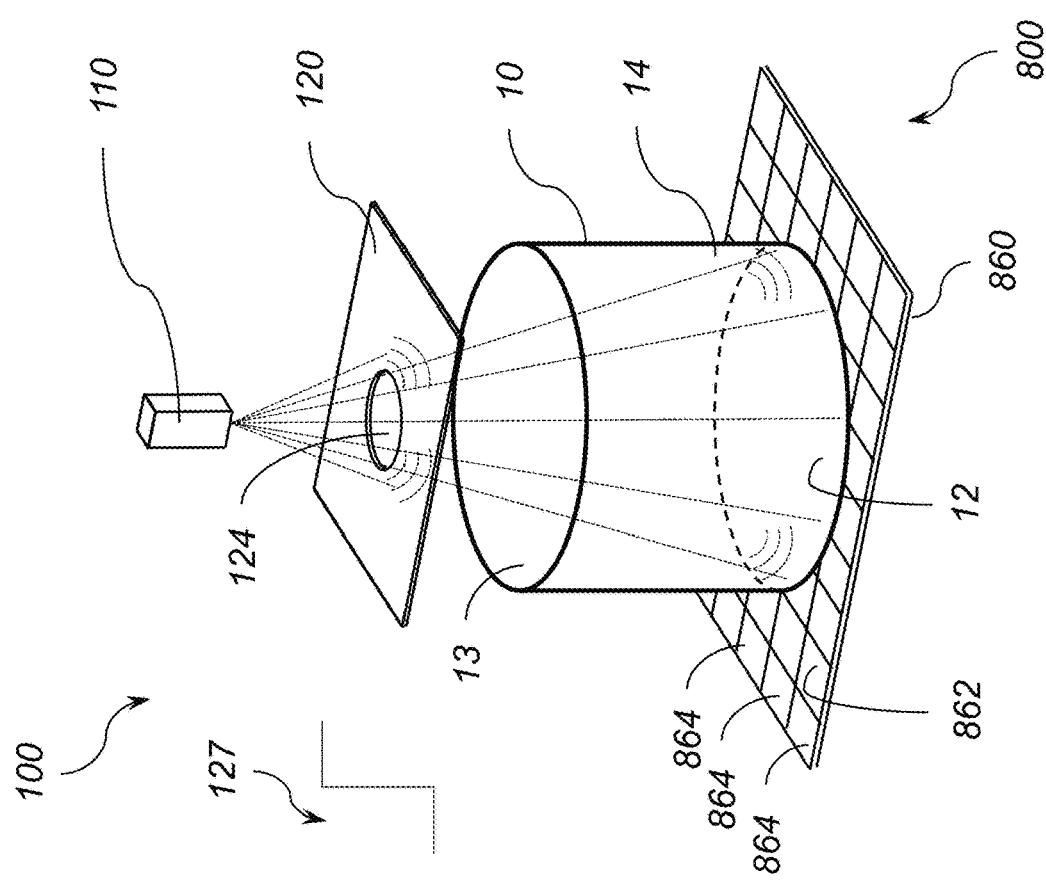
FIG. 4B illustrates an imaging system comprising an illumination system with a gradient filter providing a soft edged mask, for illumination of a sample in the container.

FIG. 4B illustrates an imaging system 800 comprising an illumination system 200 for illumination of a sample in the container 10, according to an embodiment. The illumination system 200 comprises a light source 210 and a mask 220 configured such that the projection of the light onto a plane of the bottom surface 12 of the container 10, matches the bottom surface 12 of the container 10.

The mask 220 comprises an opaque portion 222 and an at least partially transparent portion 224. In the present embodiment, the mask 220 is made of a substrate of solid, transparent material such as a glass plate, in the form of a plate. The substrate is provided with a surface coating of different light transmission properties at different portions of the substrate, so as to form a mask 220 comprising a gradient filter providing a soft edge 228 aperture at an edge of the at least partially transparent portion 224. The soft edge 228 is schematically illustrated by a gradual slope in FIG. 4B. With the mask 220 with a gradient filter providing a soft edge 228 aperture diffraction of light at the edges of the mask may be avoided. Reduction or elimination of light diffraction at the mask 220 edges may further reduce disturbing interference inside the container 10, thereby providing an illumination system 200 suitable for imaging of samples in the container 10. The interference pattern detected by the detector 860 comprising an array 862 of light sensitive areas 864 therefore provides a higher quality holographic image of the sample.

Figure 5B:
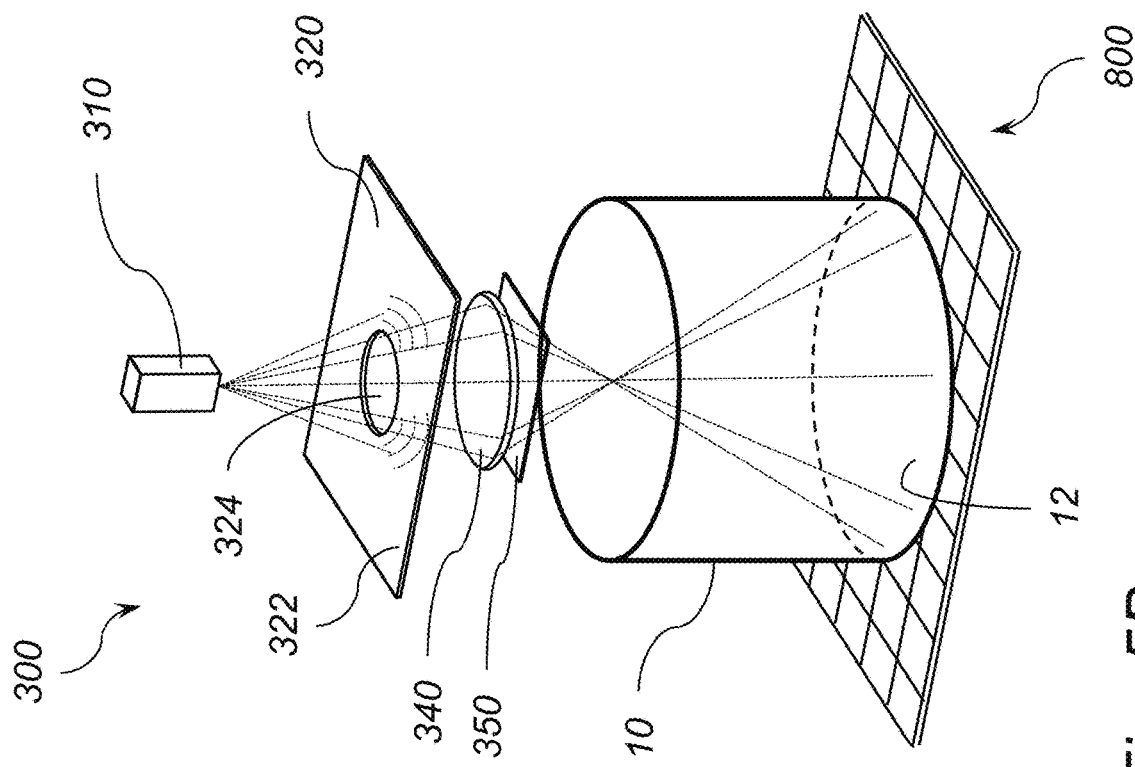
FIG. 5B illustrates an imaging system comprising an illumination system wherein the mask comprises a lens as well as an intensity filter.
Figure 5A:
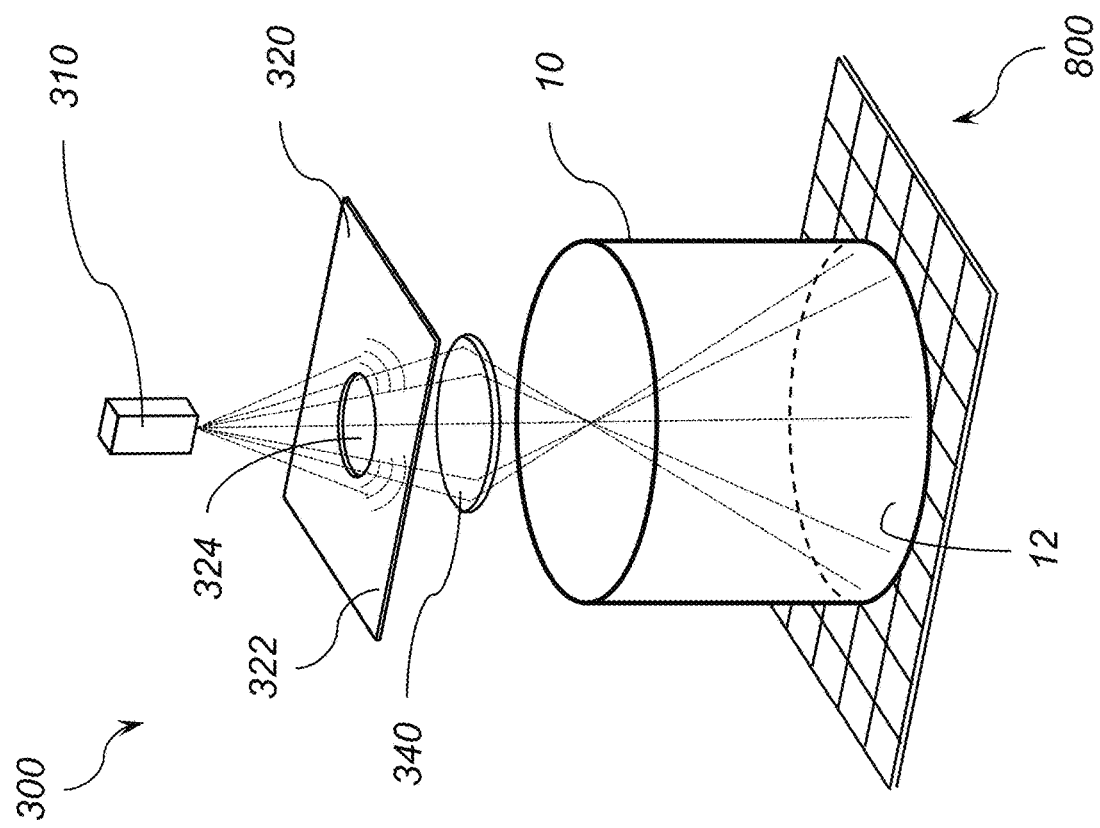
FIG. 5A illustrates an imaging system comprising an illumination system wherein the mask comprises a lens configured to reduce the effects of light diffracted at sharp mask edges.

FIGS. 5A-5B illustrates an imaging system 800 comprising an illumination system 300 wherein the mask 320 comprises a lens 340 configured to reduce the effects of light diffracted at sharp mask edges, according to an embodiment.

The illumination system 300 comprises a light source 310 and a mask 320 configured such that the projection of the light onto a plane of the bottom surface 12 of the container 10, matches the bottom surface 12 of the container 10.

The mask 320 comprises an opaque portion 322 and an at least partially transparent portion 324. In the present embodiment, the opaque portion 322 is made of a metal plate and the at least partially transparent portion 324 comprises a through hole through the metal plate. A through hole will provide a sharp edge between the opaque portion 322 and the at least partially transparent portion 324, which may give rise to light diffraction when light from the light source passes through the mask 320. It should be understood that in the mask 320 providing a sharp edge may made in alternative manners, such as for example a solid glass plate provided with a surface coating for the opaque portion 322.

The mask 320 may further comprise at least one lens 340, in the present embodiment one lens 340, arranged to direct the light from the light source 310 being passed through the mask 320 onto the bottom surface 12 of the container 10. Relaying the light from the light source 310 onto the bottom surface 12 of the container 10 by using the lens 340, may have the effect that light not coming directly from the light source 130 may be filtered out. More specifically, by using the lens 340 the diffracted light originating from sharp edges of the mask 320 may be filtered out, and thereby not reaching into the bottom surface 12 of the container 10. Thus, even if light may be diffracted at sharp edges of the mask 320, diffracted light as a source of disturbing interference may be reduced or eliminated.

FIG. 5B illustrates an imaging system 800 comprising an illumination system 300 wherein the mask 320 comprises a lens 340 as well as an intensity filter 350, according to an embodiment.

When illuminating a sample in a container 10 it may be challenging to achieve homogeneous illumination across the full width of the container 10, i.e. across the full bottom surface 12. A typical effect is that the illumination may be stronger close to the center of the bottom surface 12 and weaker closer to the outer edges of the bottom surface 12. The effect may be different for different set-ups and geometries. In case the illumination inhomogeneity across the bottom surface 12 of the container 10 is significant, uniform image quality may not be obtained.

By arranging a custom-made intensity filter 350 in the optical path of the light generated by the light source 310 being passed through the mask 320, illumination inhomogeneity may be compensated for. The intensity filter 350 may comprise different absorption coefficients across a cross-sectional plane of the optical path, thereby configured to provide a uniform illumination intensity onto the sample and the bottom surface 12 of the container 10.

According to the present embodiment, the intensity filter 350 may be optionally inserted into or ejected from the illumination system 300, by an operator. It is however conceivable that the intensity filter 350 may alternatively be arranged on the mask 320, either as a part integrated into the mask 320 or as an optionally insertable part. It is further conceivable that the intensity filter 350 may be combined with a gradient filter of a mask providing a soft edge, thus custom-made on the same substrate.

It should be understood that the intensity filter 350, although illustrated here for use in combination with the lens 340, may be combined also with other embodiments.

Figure 6:
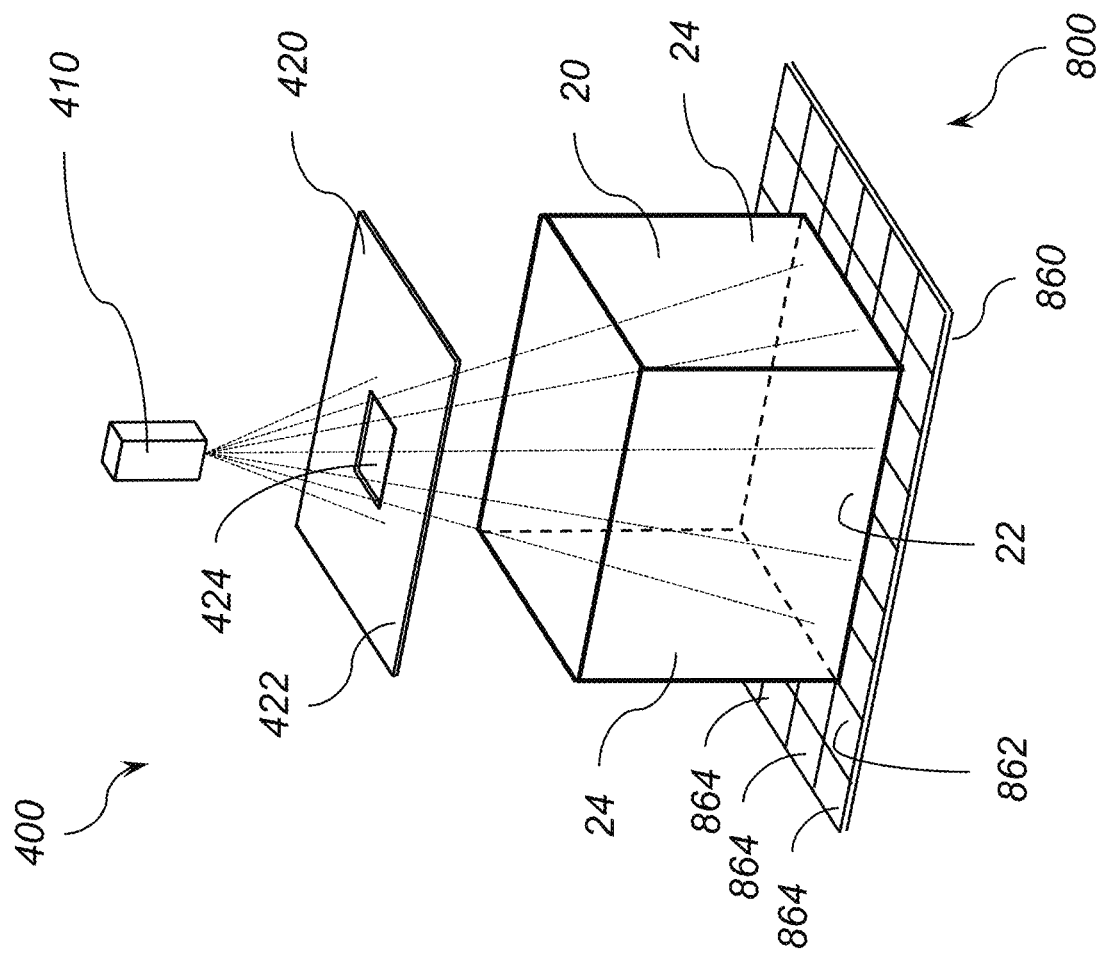
FIG. 6 illustrates an imaging system comprising the illumination system for illumination of a sample in the container with a bottom surface having a square shape.

FIG. 6 illustrates an imaging system 800 comprising the illumination system 400 for illumination of a sample in the container 20 with a bottom surface 22 having a square shape, according to an embodiment.

The illumination system 400 comprises a light source 410 and a mask 420 configured such that the projection of the light onto a plane of the bottom surface 12 of the container 10, matches the square shape of the bottom surface 12 of the container 10. The size of the container 20 may be different for different containers 20, but the illumination system is configured such that the projection of the light onto the plane of the bottom surface 22 of the container 20 may be adapted to match a square shape having a size of a side in a range of 10 μm to 150 mm.

According to the present embodiment, since the mask 420 is arranged to be parallel with the bottom surface 22 of the container 20, the at least partially transparent portion 424 of the mask 420 has the shape of a square as well. However, in an alternative where the mask 420 is arranged at an angle with respect to the bottom surface 22, the shape of the at least partially transparent portion 424 may differ from a square.

In the present manner, a sample in the container 20 may be illuminated by the light from the light source 410, yet illumination of the side walls 24 may be avoided.

The detector 860 is arranged below the bottom surface 22 of the container 20, with the array 862 of light sensitive areas 864 facing the bottom surface 22 of the container 20.

Scattered light from the sample and non-scattered light, from the same light source 410, is transmitted to the array 862 of light sensitive areas 864, forming an interference pattern in the plane of the array 862. The array 862 of light sensitive areas 864 is configured to detect the interference pattern, so as to image the sample.

By detection and acquisition of the interference pattern, information about the three-dimensional shape of the sample is acquired in terms of a digital hologram such that a high-resolution image of the sample may be generated by holographic reconstruction.

Figure 7B:
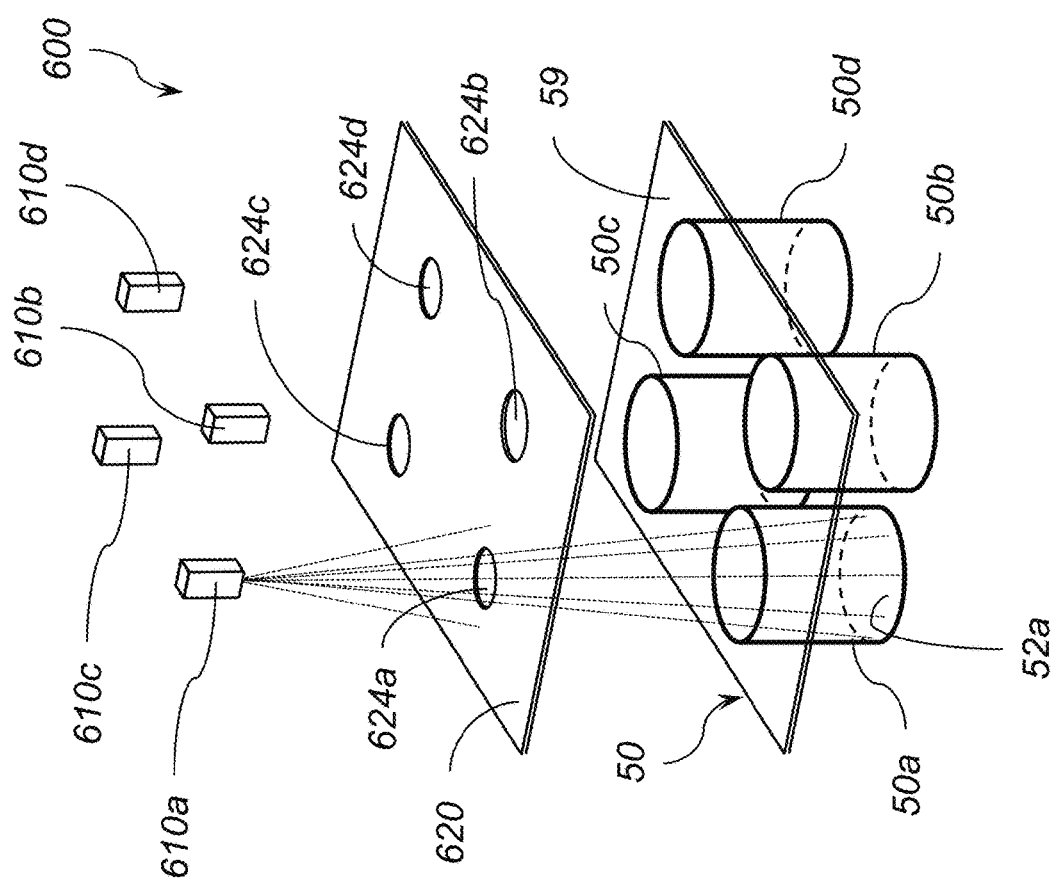
FIG. 7B illustrates an illumination system configured for illumination of a sample in an array of containers by multiple light sources and a mask with multiple at least partially transparent portions.
Figure 7A:
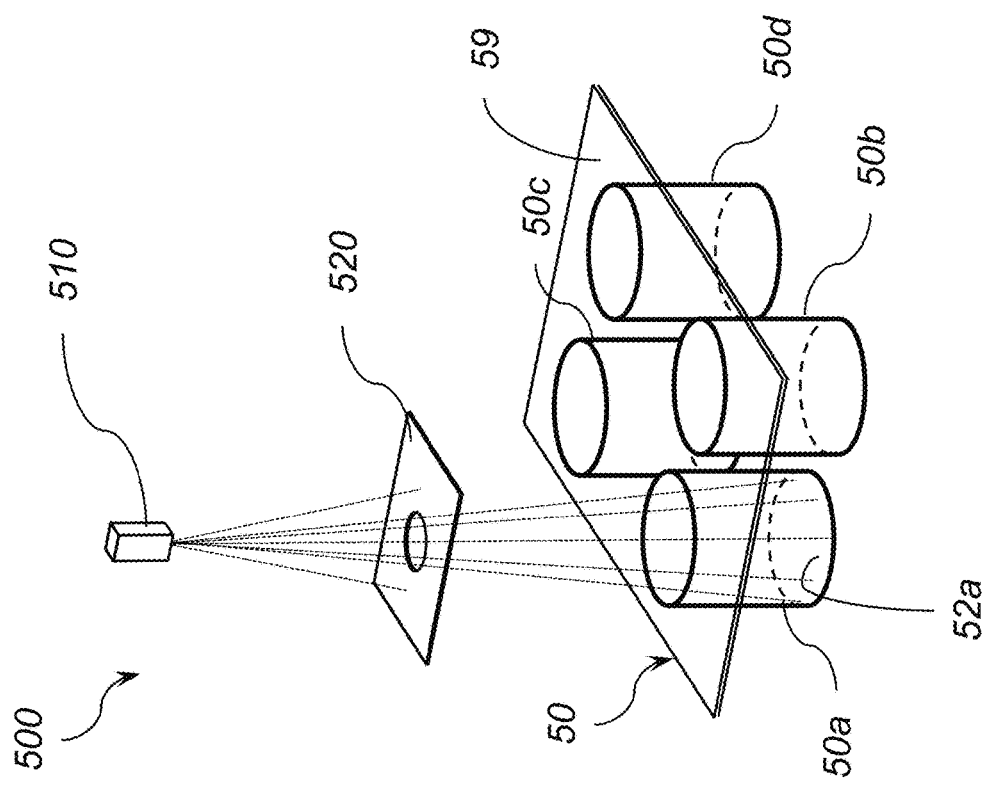
FIG. 7A illustrates an illumination system configured for illumination of a sample in an array of containers by a movable light source and mask.

FIG. 7A illustrates an illumination system 500 configured for illumination of a sample in an array of containers 50, according to an embodiment.

The array of containers 50 in the present embodiment is a microplate, and more specifically a 4-well plate. Thus, the array of containers 50 comprises four individual containers 50a, 50b, 50c, 50d combined on a common support plate 59. However, it is conceivable that the array of containers 50 alternatively may be of another type, such as any other type of microplate.

According to the present embodiment, the light source 510 and the mask 520 are jointly movable in relation to the array of containers 50. Movement of the light source 510 and the mask 520 in relation to the array of containers 50 may be achieved in a number of different manners. By way of example, movement of the light source 510 and the mask 520 in relation to the array of containers 50 may be achieved by an actuator arrangement (not shown in FIG. 7A) similar to the arrangement illustrated in FIG. 3. Such an actuator arrangement may serve the purpose of moving the light source 510 and mask 520 from one container 50*a* to the next container 50*b*, as well as of adjusting the position of the light source 510 and mask 520 in relation to a container 50*a* in order to provide matching of the projection of light to the bottom surface 52*a* of the container 50*a*. By the present arrangement, the light source 510 and the mask 520 may be moved between positions configured to be associated with illumination of different containers 50*a*, 50*b*, 50*c*, 50*d* in the array of containers 50.

However, it is also conceivable that the light source 510 and the mask 520 are moved in relation to the array of containers 50 by an alternative arrangement which moves the array of containers 50 in relation to a stationary light source 510 and mask 520.

FIG. 7B illustrates an illumination system 600 configured for illumination of a sample in an array of containers 50, according to an embodiment.

The illumination system 600 comprises a plurality of light sources 610*a*, 610*b*, 610*c*, 610*d* and a mask 620 comprises a plurality of at least partially transparent portions 624*a*, 624*b*, 624*c*, 624*d* such that different pairs of one light source 610*a*, 610*b*, 610*c*, 610*d* and one at least partially transparent portion 624*a*, 624*b*, 624*c*, 624*d* are configured to be associated with different containers 50*a*, 50*b*, 50*c*, 50*d* in the array of containers 50.

According to the present embodiment, neither the mask 620 nor the light sources 610*a*, 610*b*, 610*c*, 610*d* need to be moved in order to be positioned for illumination of samples in each of the individual containers 50*a*, 50*b*, 50*c*, 50*d*. By way of example, the illumination system may be stationary, into which arrays of containers 50 may be placed, one by one, and the samples in the containers 50*a*, 50*b*, 50*c*, 50*d* may be illuminated, either sequentially or simultaneously. After all containers 50*a*, 50*b*, 50*c*, 50*d* are handled, the array of containers 50 may be removed and a new array of containers 50 may be inserted for illumination.

As an alternative, it is conceivable that the mask 620 comprises a plurality of at least partially transparent portions 624*a*, 624*b*, 624*c*, 624*d*, but instead of the illumination system 600 comprising a plurality of light sources 610*a*, 610*b*, 610*c*, 610*d*, the illumination system 600 comprises only one light source 610 being movable in relation to the mask 620. In the present manner, the light source 610 may move to positions above the at least partially transparent portions 624*a*, 624*b*, 624*c*, 624*d*, associated with different containers 50*a*, 50*b*, 50*c*, 50*d* in the array of containers 50.

Figure 8:
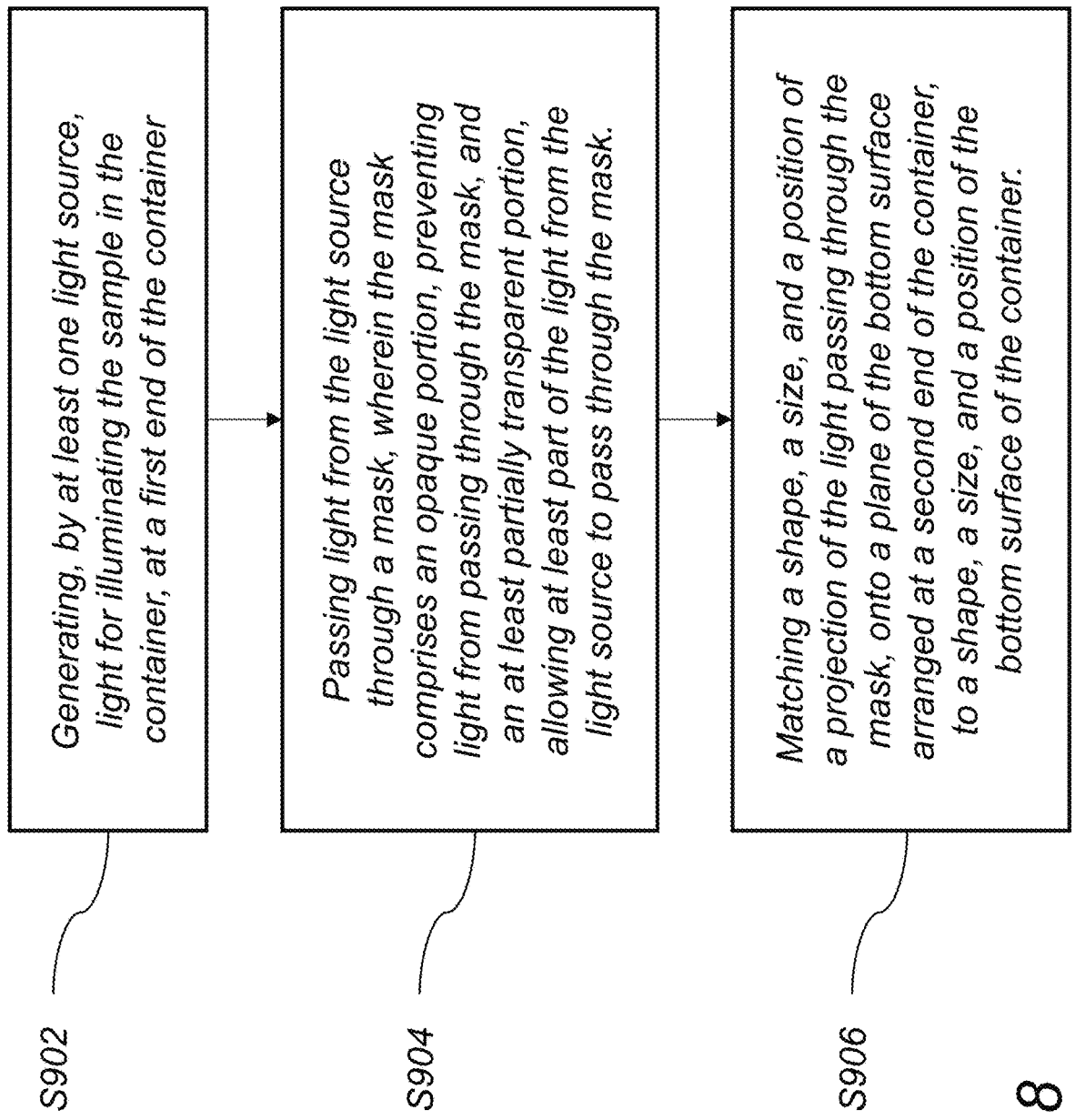
FIG. 8 illustrates a schematic block diagram shortly summarizing the method for illumination of a sample in a container as described in relation to the illumination systems and the imaging system.

FIG. 8 illustrates a schematic block diagram shortly summarizing the method for illumination of a sample in a container as previously described in relation to the illumination systems 100, 200, 300, 400, 500, 600 and the imaging system 800. It should be understood that the steps of the method, although listed in a specific order herein, may be performed in any order suitable.

The method is intended for illumination of containers such as wells of a microplates or petri dishes, wherein the container comprises a bottom surface and side walls which together define a volume for receiving samples.

The method may comprise generating S902, by at least one light source, light for illuminating the sample in the container, at a first end of the container.

The method may comprise passing S904 light from the light source through a mask, wherein the mask comprises an opaque portion, preventing light from passing through the mask, and an at least partially transparent portion, allowing at least part of the light from the light source to pass through the mask.

The method may comprise matching S906 a shape, a size, and a position of a projection of the light passing through the mask, onto a plane of the bottom surface arranged at a second end of the container, to a shape, a size, and a position of the bottom surface of the container.

In the above the inventive concept has mainly been described with reference to a limited number of embodiments. However, as is readily appreciated by a person skilled in the art, other embodiments than the ones disclosed above are equally possible within the scope of the inventive concept, as defined by the appended claims.

The invention claimed is:

1. An illumination system for illumination of a sample in a container, such as a well of a microplate or a petri dish, the container comprising a bottom surface and side walls which together define a volume for receiving the sample, the illumination system comprising:
    at least one light source being configured to generate light;
    a mask arranged such that light from the light source impinges onto the mask, wherein the mask comprises an opaque portion, preventing light from passing through the mask, and an at least partially transparent portion, allowing at least part of the light from the light source to pass through the mask;
    wherein the illumination system is adapted to be positioned at a first end of the container such that the light generated by the light source, passing through the mask, illuminates the sample in the container; and
    wherein the at least one light source and the mask are configured for light generated by the at least one light source being passed through the mask such that a shape, a size, and a position of a projection of the light passing through the mask, onto a plane of the bottom surface arranged at a second end of the container, opposite to the first end, match a shape, a size, and a position of the bottom surface of the container.

2. The illumination system according to claim 1, wherein the at least one light source and the mask are configured for the shape, the size, and the position of the projection of the light passing through the mask, onto the plane of the bottom surface of the container, to match the shape, the size, and the position of the bottom surface of the container, by a position of the at least one light source being adjustable relative to the container and/or a position of the mask being adjustable relative to the container and/or the at least one light source.

3. The illumination system according to claim 1, wherein the opaque portion of the mask is made of a solid material and the at least partly transparent portion of the mask comprises a through hole.

4. The illumination system according to claim 1, wherein the mask is made of a solid, transparent material provided with at least one surface coating.

5. The illumination system according to claim 1, wherein the mask comprises a gradient filter providing a soft edge aperture at an edge of the at least partially transparent portion.

6. The illumination system according to claim 1, wherein the mask comprises at least one lens arranged to direct the light being passed through the mask onto the bottom surface of the container.

7. The illumination system according to claim 1, further comprising an intensity filter arranged in an optical path of the light generated by the light source being passed through the mask, the intensity filter comprising different absorption coefficients across a cross-sectional plane of the optical path, thereby configured to provide a uniform illumination intensity onto the bottom surface of the container.

8. The illumination system according to claim 7, wherein the intensity filter is arranged on the mask.

9. The illumination system according to claim 7, wherein a shape of the at least partially transparent portion of the mask matches the shape of the bottom surface of the container.

10. The illumination system according to claim 1, wherein the mask is arranged to extend in a plane parallel to the plane of the bottom surface of the container.

11. The illumination system according to claim 1, wherein the at least one light source and the mask are configured for the shape and the size of the projection of the light passing through the mask, onto the plane of the bottom surface of the container, to match a circular shape having a diameter in a range of 10 µm to 150 mm.

12. The illumination system according to claim 1, wherein the at least one light source and the mask are configured for the shape and the size of the projection of the light passing through the mask, onto the plane of the bottom surface of the container, to match a square shape having a size of a side in a range of 10 µm to 150 mm.

13. The illumination system according to claim 1, wherein the illumination system is configured for illumination of samples in an array of containers, by the at least one light source and the mask being configured to be jointly movable in relation to the array of containers for moving the at least one light source and the mask between positions configured to be associated with illumination of different containers in the array, or by the at least one light source being movable in relation to the mask, wherein the mask comprises a plurality of at least partially transparent portions configured to be associated with different containers in the array, or by the illumination system comprising a plurality of light sources and the mask comprising a plurality of at least partially transparent portions such that different pairs of one light source and one at least partially transparent portions are configured to be associated with different containers in the array.

14. An imaging system for imaging a sample in a container, the imaging system comprising:
   the illumination system according to claim 1;
   a detector comprising an array of light sensitive areas;
   wherein the imaging system is further configured such that at least part of the light illuminating the sample is scattered by the sample, forming scattered light;
   wherein the imaging system is further configured to transmit the scattered light and non-scattered light, from the same light source, to the array of light sensitive areas, wherein the array of light sensitive areas is configured to detect an interference pattern formed by interference between the scattered light and the non-scattered light, so as to image the sample.

15. A method for illumination of a sample in a container, such as a well of a microplate or a petri dish, the container comprising a bottom surface and side walls which together define a volume for receiving the sample, the method comprising:
   generating, by at least one light source, light for illuminating the sample in the container, at a first end of the container;
   passing light from the light source through a mask, wherein the mask comprises an opaque portion, preventing light from passing through the mask, and an at least partially transparent portion, allowing at least part of the light from the light source to pass through the mask;
   wherein the at least one light source and the mask are configured for light generated by the at least one light source being passed through the mask such that a shape, a size, and a position of a projection of the light passing through the mask, onto a plane of the bottom surface arranged at a second end of the container, opposite to the first end, match a shape, a size, and a position of the bottom surface of the container.

* * * * *